(12) United States Patent
DiClaudio

(10) Patent No.: US 11,660,428 B2
(45) Date of Patent: May 30, 2023

(54) MEDICAL BALLOONS, BALLOON CATHETERS, AND METHODS THEREOF

(71) Applicant: C.R. BARD, INC., Murray Hill, NJ (US)

(72) Inventor: Karen A. DiClaudio, Tempe, AZ (US)

(73) Assignee: C.R. BARD, INC., Franklin Lakes, NJ (US)

( * ) Notice: Subject to any disclaimer, the term of this patent is extended or adjusted under 35 U.S.C. 154(b) by 904 days.

(21) Appl. No.: 16/469,344

(22) PCT Filed: Dec. 12, 2017

(86) PCT No.: PCT/US2017/065901
§ 371 (c)(1),
(2) Date: Jun. 13, 2019

(87) PCT Pub. No.: WO2018/111932
PCT Pub. Date: Jun. 21, 2018

(65) Prior Publication Data
US 2020/0009356 A1    Jan. 9, 2020

Related U.S. Application Data

(60) Provisional application No. 62/435,226, filed on Dec. 16, 2016.

(51) Int. Cl.
*A61M 25/10* (2013.01)
*A61L 29/12* (2006.01)
*A61L 29/14* (2006.01)

(52) U.S. Cl.
CPC ....... *A61M 25/1029* (2013.01); *A61L 29/126* (2013.01); *A61L 29/143* (2013.01);
(Continued)

(58) Field of Classification Search
CPC .......... A61M 25/0009; A61M 25/0012; A61M 25/005; A61M 25/10; A61M 25/1018;
(Continued)

(56) References Cited

U.S. PATENT DOCUMENTS

| 5,330,429 A | 7/1994 | Noguchi et al. |
| 2006/0079836 A1* | 4/2006 | Holman ............ A61M 25/1002 604/510 |

(Continued)

FOREIGN PATENT DOCUMENTS

| CN | 201366175 Y | 12/2009 |
| CN | 105025968 A | 11/2015 |

(Continued)

OTHER PUBLICATIONS

English Translation of CN105025968A1 dated Nov. 4, 2015.
English Translation of CN201366175Y dated Dec. 23, 2009.

*Primary Examiner* — Robert A Lynch
(74) *Attorney, Agent, or Firm* — Dickinson Wright PLLC; Andrew D. Dorisio

(57) ABSTRACT

Provided herein in some embodiments is an apparatus including a composite balloon with a tubular fiber layer and a polymeric balloon layer over the fiber layer. Also provided herein in some embodiments is a method including inserting a collapsed fiber tube into an expanded polymeric balloon, expanding the collapsed fiber tube to provide an expanded fiber tube, and securing an outer surface of the expanded fiber tube to an inner surface of the expanded polymeric balloon. The method can further include inserting a distal portion of an elongate catheter body through a center of the composite balloon and securing the composite balloon to the distal portion. Thereby, the method can include forming the catheter body with the composite balloon configured to apply a pressure to surrounding walls of an anatomical (Continued)

Figure 1A:
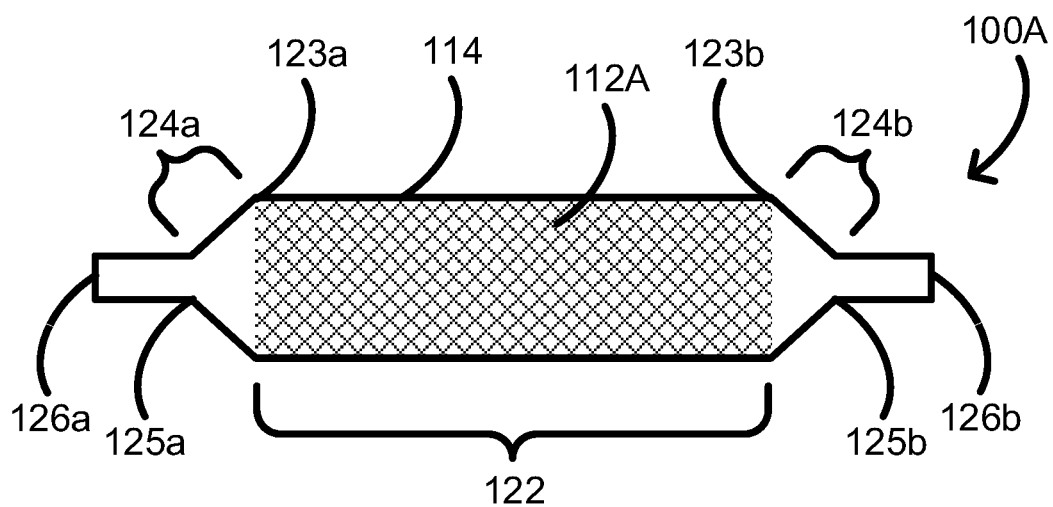

vessel in an inflated state of the composite balloon to modify one or more intravascular lesions in the anatomical vessel.

21 Claims, 9 Drawing Sheets

(52) U.S. Cl.
CPC .... *A61M 25/104* (2013.01); *A61M 25/10181* (2013.11); *A61M 2025/1031* (2013.01); *A61M 2025/1075* (2013.01); *A61M 2025/1084* (2013.01)

(58) Field of Classification Search
CPC ...... A61M 25/10181; A61M 25/10184; A61M 25/1027; A61M 25/1029; A61M 25/1034; A61M 25/1036; A61M 25/104; A61M 2025/1031; A61M 2025/1043; A61M 2025/1056; A61M 2025/1063; A61M 2025/1068; A61M 2025/1075; A61M 2025/1084; A61M 2025/1086; A61M 2025/1088; A61L 29/126; A61L 29/143
See application file for complete search history.

(56) References Cited

U.S. PATENT DOCUMENTS

| | | | |
|---|---|---|---|
| 2007/0250101 A1* | 10/2007 | Horn | B32B 5/22 606/192 |
| 2008/0033477 A1* | 2/2008 | Campbell | A61M 25/104 606/194 |
| 2008/0183132 A1* | 7/2008 | Davies | A61M 25/104 604/103.09 |
| 2009/0038752 A1 | 2/2009 | Weng et al. | |
| 2009/0227947 A1* | 9/2009 | Caclin | A61M 25/10182 604/97.02 |
| 2009/0294031 A1 | 12/2009 | Pepper et al. | |
| 2011/0264039 A1 | 10/2011 | Thielen et al. | |
| 2012/0330232 A1* | 12/2012 | Hedberg | A61M 25/104 604/103.05 |
| 2015/0272732 A1* | 10/2015 | Tilson | A61F 2/958 623/2.11 |
| 2018/0036518 A1* | 2/2018 | Yang | A61M 25/1029 |

FOREIGN PATENT DOCUMENTS

| | | |
|---|---|---|
| JP | 2010115375 A | 5/2010 |
| WO | 2011082637 A1 | 7/2011 |
| WO | 2015031616 A2 | 3/2015 |

* cited by examiner

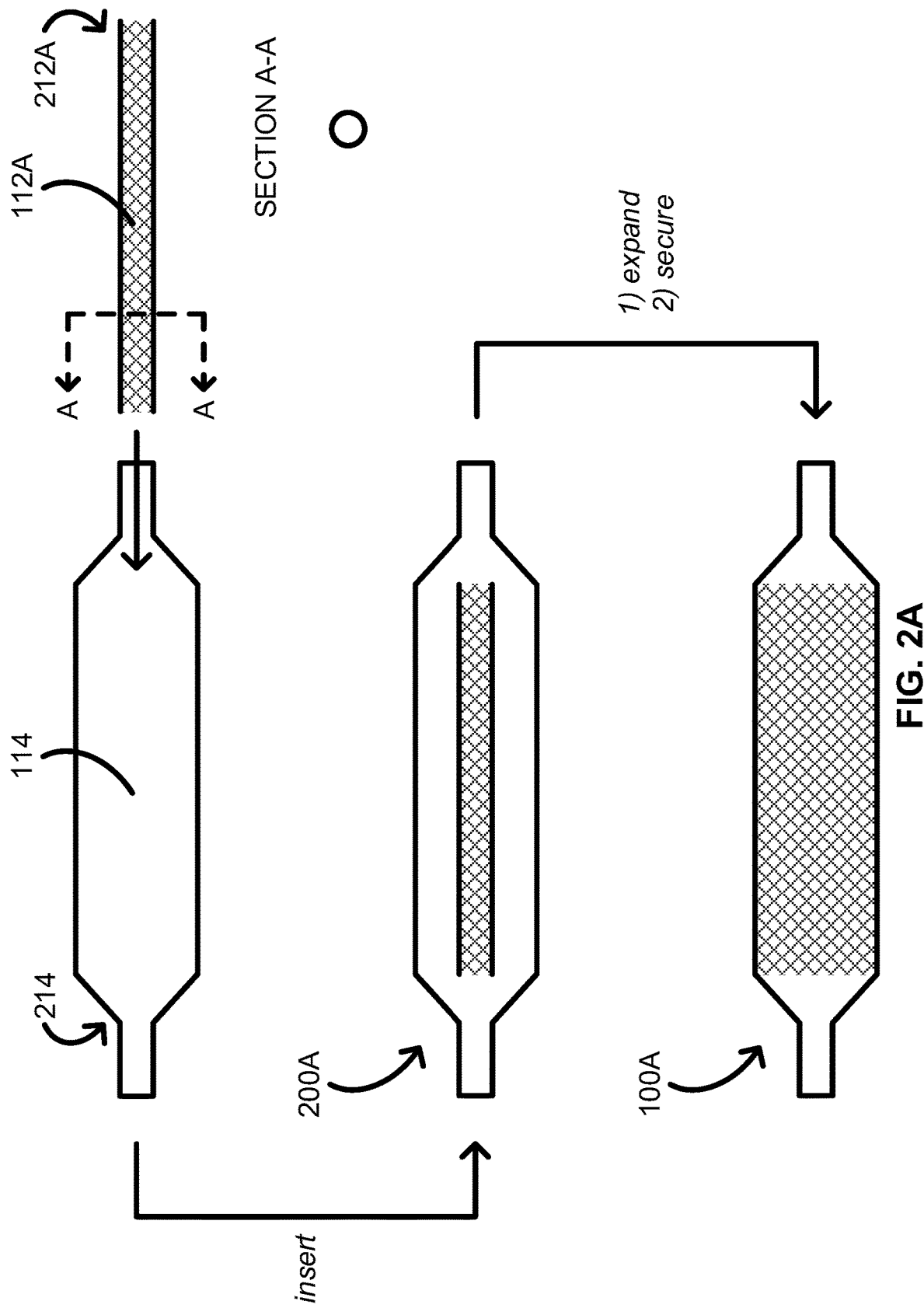

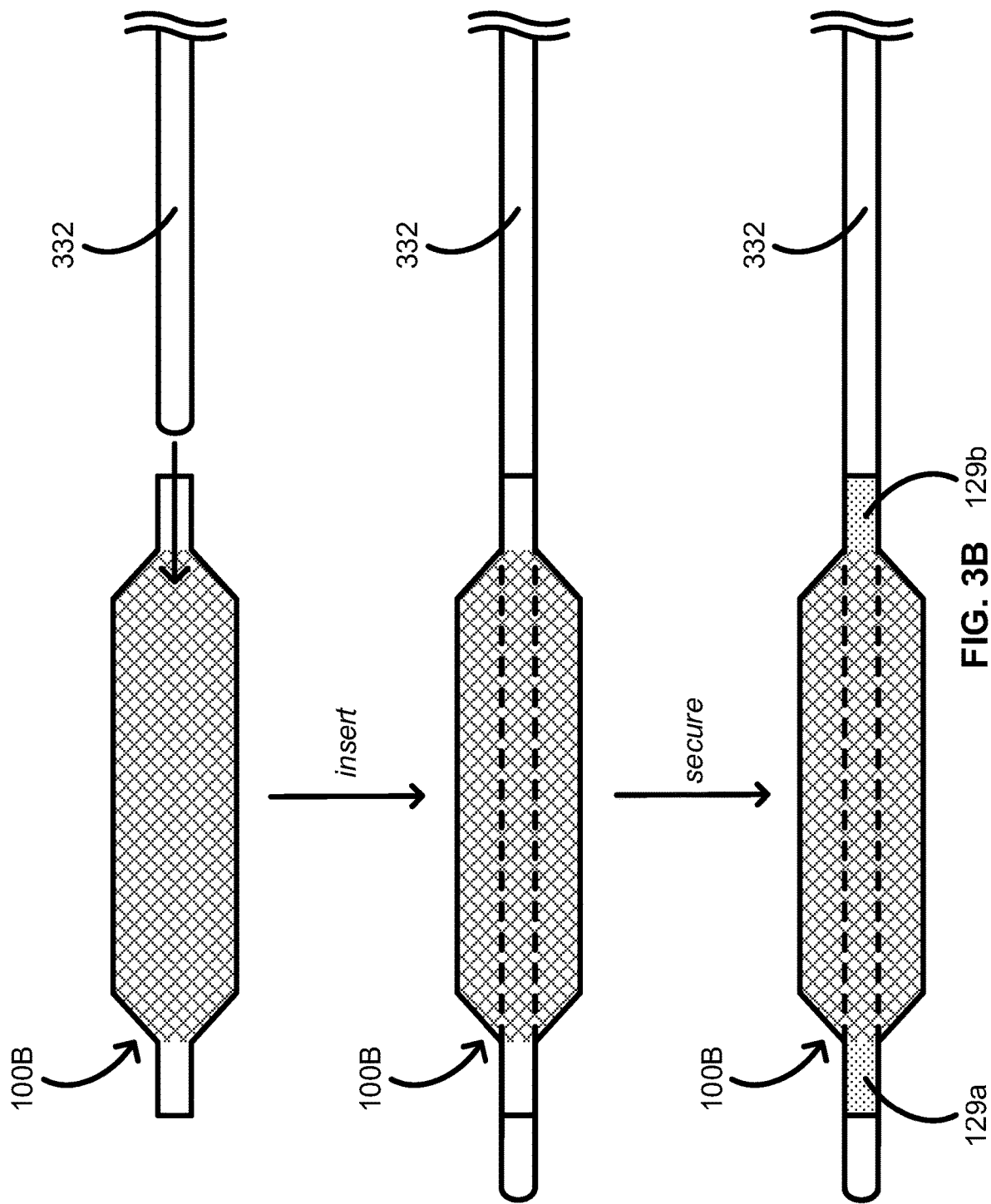

MEDICAL BALLOONS, BALLOON CATHETERS, AND METHODS THEREOF

PRIORITY

This application claims the benefit of priority to U.S. Provisional Application No. 62/435,226, filed Dec. 16, 2016, which is incorporated by reference in its entirety into this application.

FIELD

This application generally relates to medical balloons, balloon catheters, and methods thereof.

BACKGROUND

Atherosclerosis is characterized by one or more intravascular lesions formed in part of plaque including blood-borne substances such as fat, cholesterol, and calcium. An intravascular lesion such as an arterial lesion can form on a wall of an arterial lumen and build out across the lumen to an opposite wall thereof. A last point of patency often occurs at a boundary between the arterial lesion and the opposite wall of the arterial lumen. Surgical procedures for atherosclerosis such as balloon angioplasty can be used to restore patency and blood flow lost to the one or more intravascular lesions. However, a need continues to exist for medical balloons such as angioplasty balloons having a low degree of compliance, thin walls, puncture resistance, and improved trackability. Provided herein in some embodiments are systems and methods that address the foregoing.

SUMMARY

Provided herein in some embodiments is an apparatus including a composite balloon with a tubular fiber layer and a polymeric balloon layer over the fiber layer. The composite balloon can be configured to apply a pressure to surrounding walls of an anatomical vessel in an inflated state of the composite balloon to modify one or more intravascular lesions in the anatomical vessel.

Also provided herein in some embodiments is an apparatus including an elongate catheter body; an inflation lumen disposed within the catheter body; and a composite balloon. The elongate catheter body can include a distal portion and a proximal portion, and the composite balloon can be about the distal portion. The composite balloon can include a tubularly braided fiber layer and a polymeric balloon layer over the fiber layer. The composite balloon can be configured to apply a pressure to surrounding walls of an anatomical vessel in an inflated state of the composite balloon to modify one or more intravascular lesions in the anatomical vessel.

Also provided herein in some embodiments is a method including inserting a collapsed fiber tube into an expanded polymeric balloon; expanding the collapsed fiber tube to provide an expanded fiber tube; and securing the expanded fiber tube to the expanded polymeric balloon. The expanded fiber tube can include an outer surface, and the expanded polymeric balloon can include an inner surface. Securing the expanded fiber tube to the expanded polymeric balloon can include securing the outer surface of the expanded fiber tube to the inner surface of the expanded polymeric balloon. Thereby, the method can include forming a composite balloon configured to apply a pressure to surrounding walls of an anatomical vessel in an inflated state of the composite balloon to modify one or more intravascular lesions in the anatomical vessel.

These and other features of the concepts provided herein may be better understood with reference to the drawings, description, and appended claims.

DRAWINGS

FIG. 1A provides a schematic illustrating a composite balloon in accordance with some embodiments.

Figure 1B:
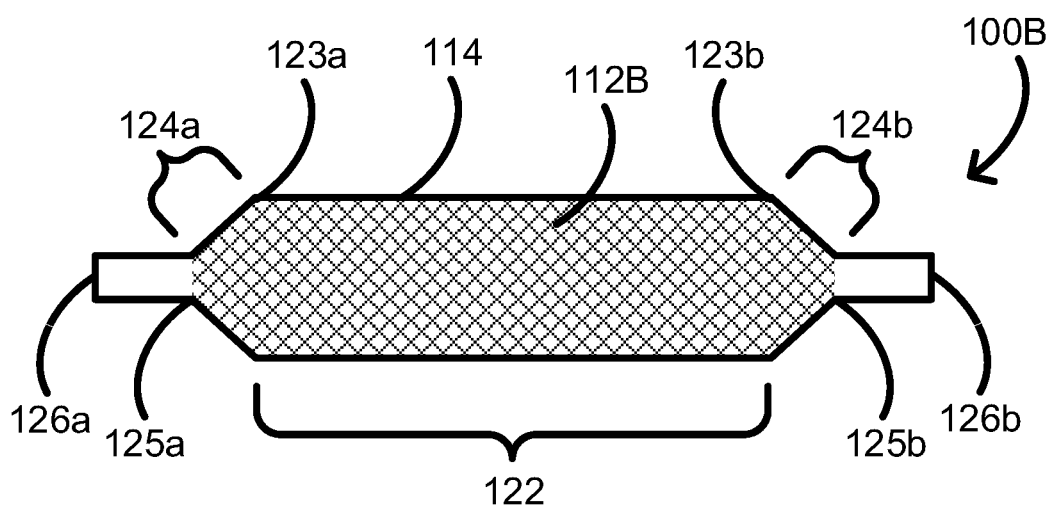

FIG. 1B provides a schematic illustrating a composite balloon in accordance with some embodiments.

FIG. 2A provides a schematic illustrating a method for producing a composite balloon in accordance with some embodiments.

Figure 2B:
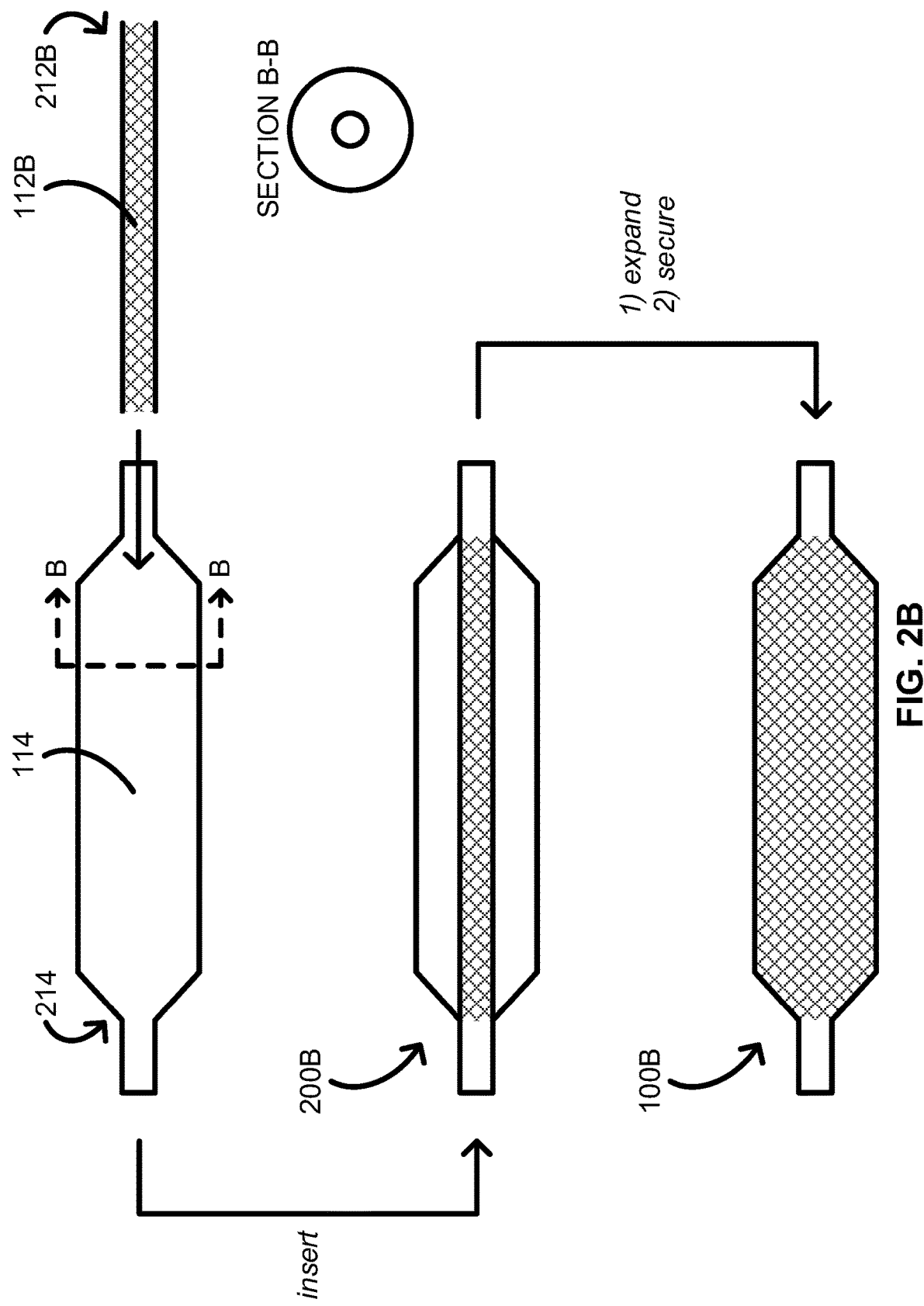

FIG. 2B provides a schematic illustrating a method for producing a composite balloon in accordance with some embodiments.

Figure 3A:
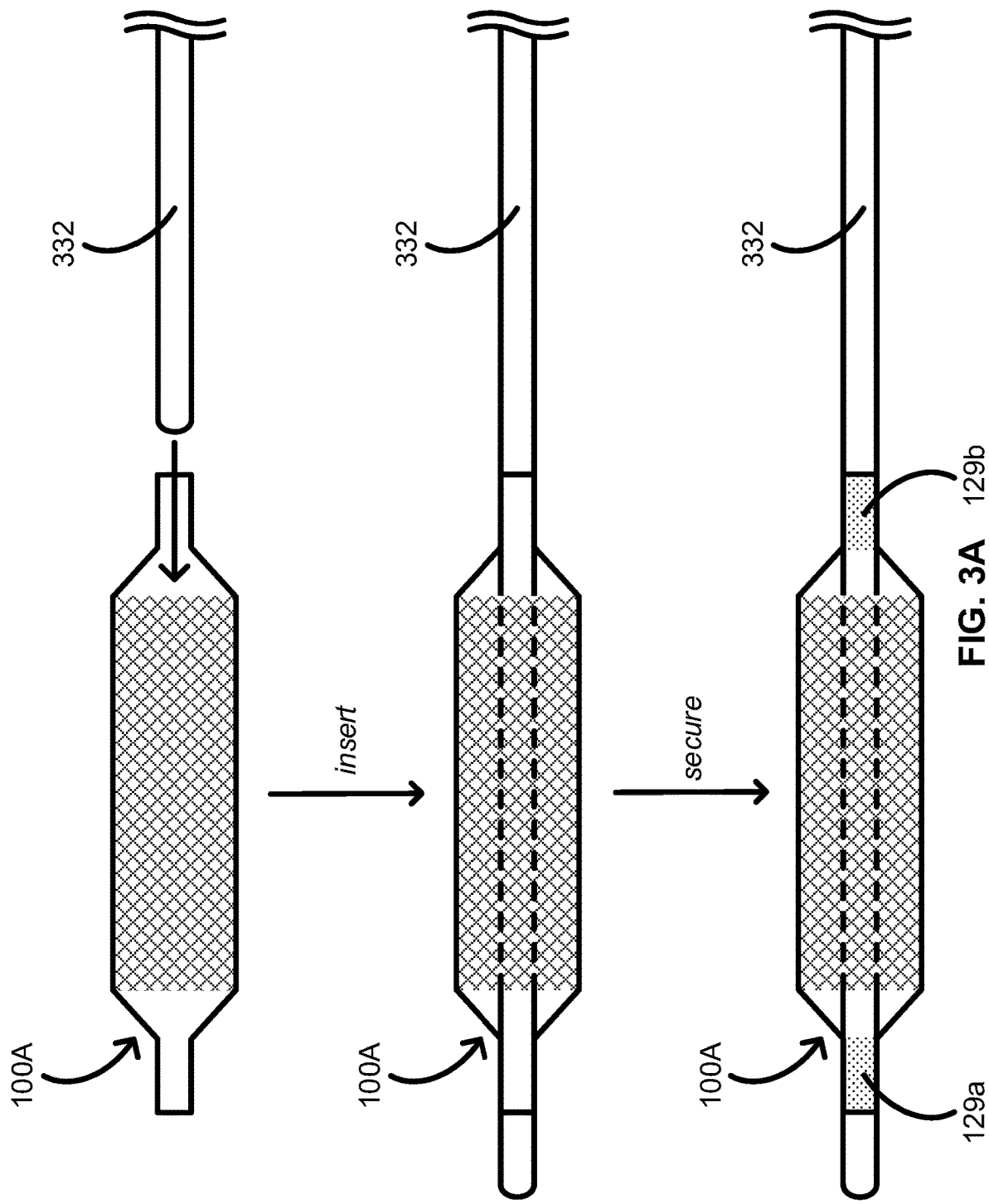

FIG. 3A provides a schematic illustrating a method for producing a catheter with a composite balloon in accordance with some embodiments.

FIG. 3B provides a schematic illustrating a method for producing a catheter with a composite balloon in accordance with some embodiments.

Figure 4A:
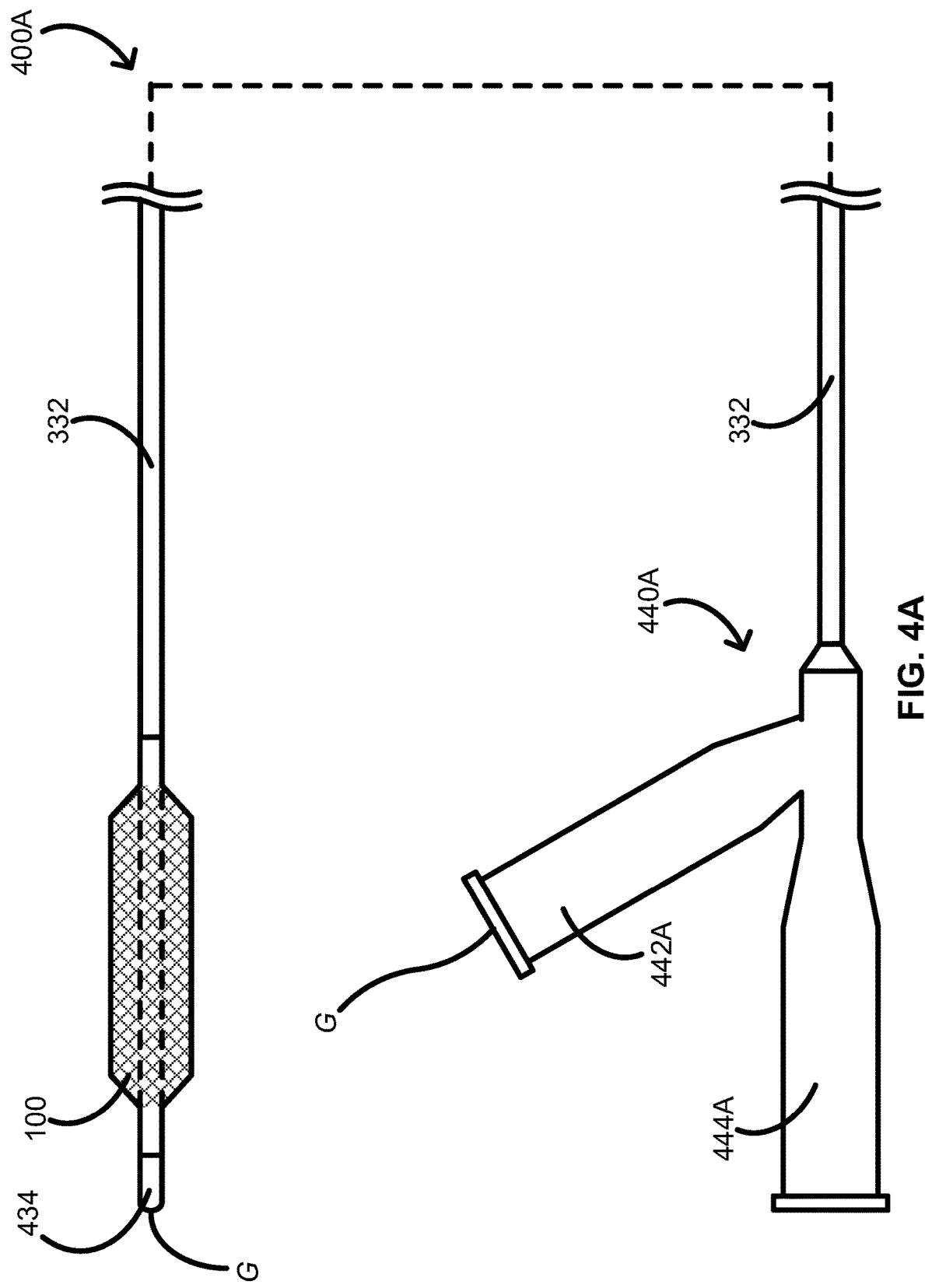

FIG. 4A provides a schematic illustrating an over-the-wire balloon catheter including a composite balloon in accordance with some embodiments.

Figure 4B:
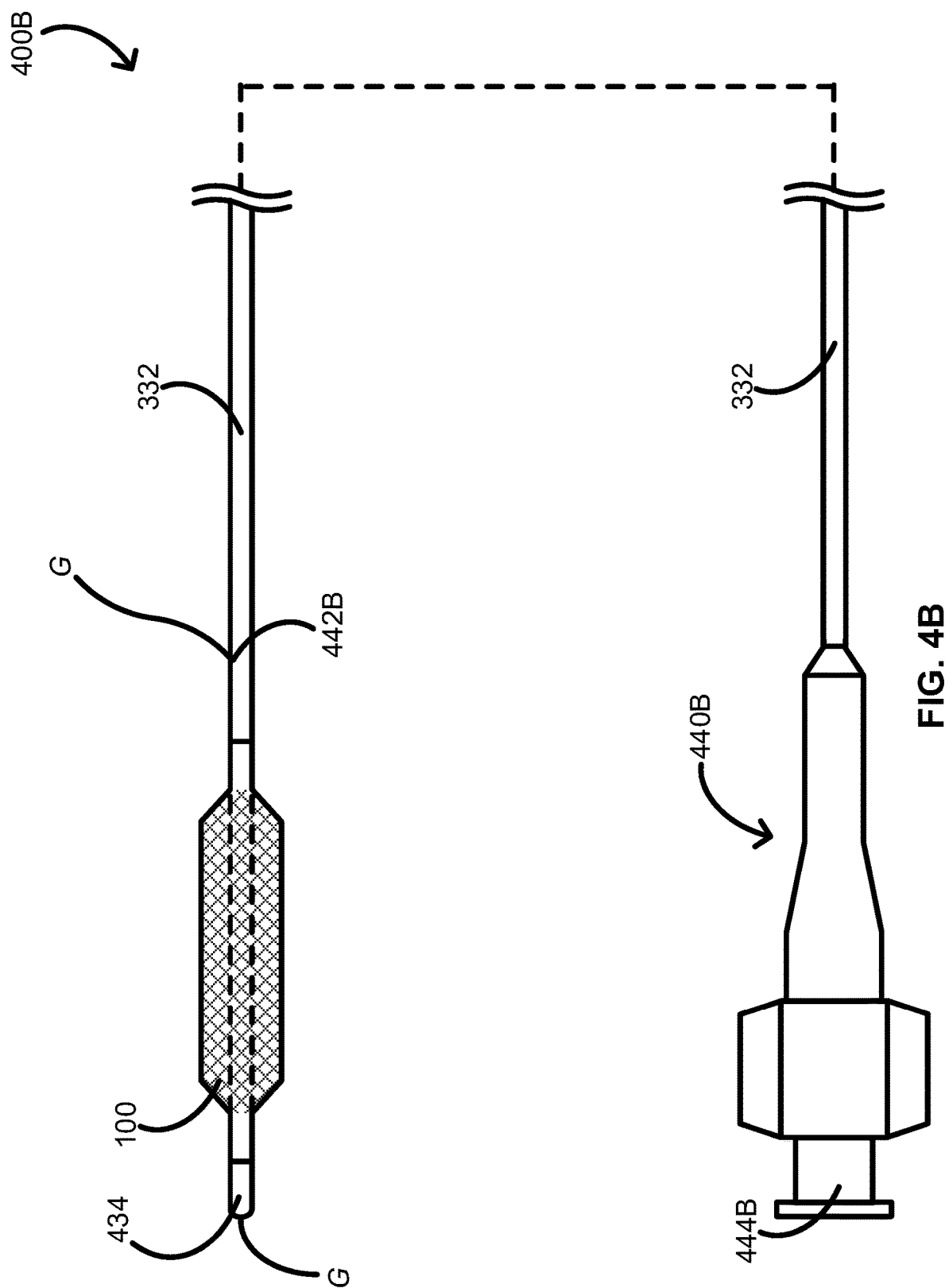

FIG. 4B provides a schematic illustrating a rapid-exchange balloon catheter including a composite balloon in accordance with some embodiments.

Figure 4C:
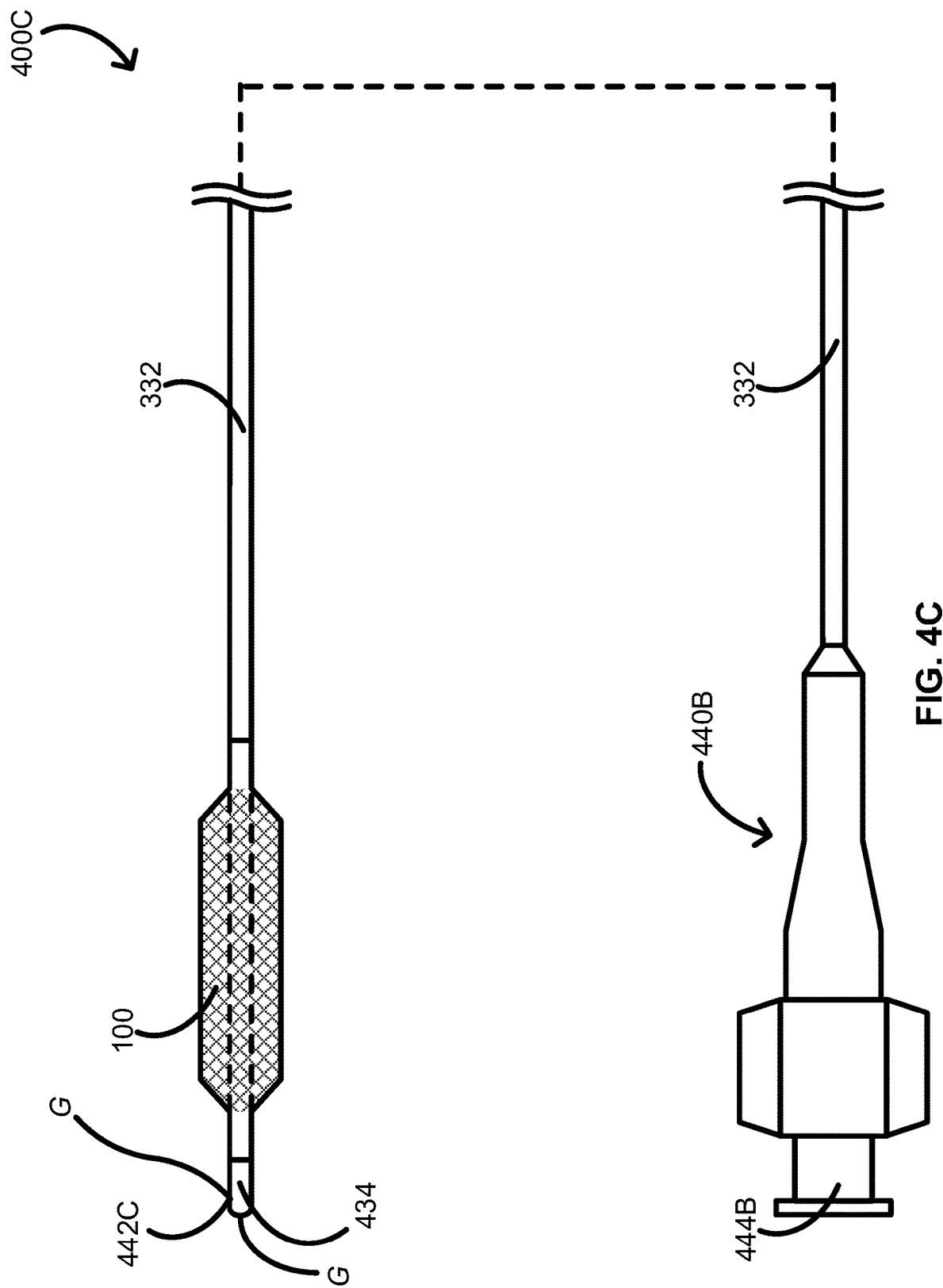

FIG. 4C provides a schematic illustrating a short rapid-exchange balloon catheter including a composite balloon in accordance with some embodiments.

Figure 5:
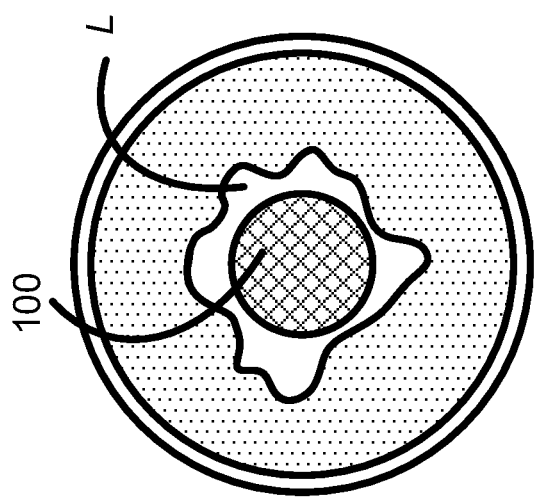
Figure 5:
Figure 5:
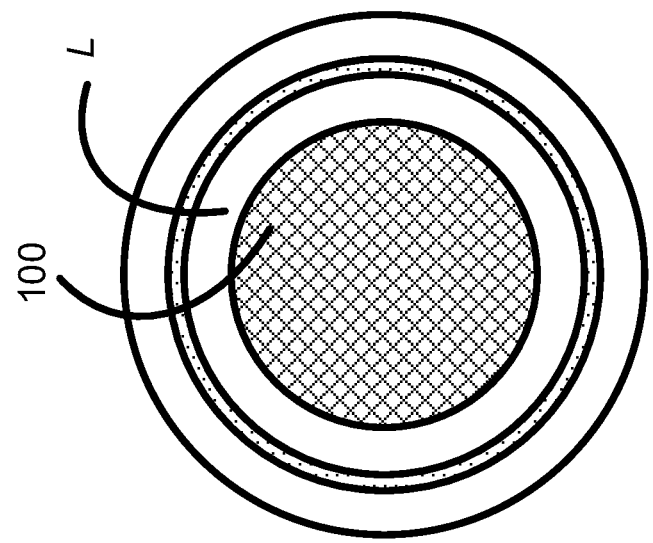

FIG. 5 provides a schematic illustrating modification of an intravascular lesion in accordance with some embodiments.

DETAILED DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Non-compliance or a low degree of compliance refers to a capability of a medical balloon to substantially maintain a predetermined size and profile under pressure without expanding beyond the predetermined size and profile. A non-compliant medical balloon is less likely to rupture or dissect an anatomical vessel as the medical balloon expands.

Trackability refers to a capability of a medical balloon to traverse a tortuous path through anatomical vessels, body cavities, occlusions, or a combination thereof. Flexible medical balloons generally provide better trackability. A high degree of trackability is desirable.

Unless defined otherwise, all technical and scientific terms used herein have the same meaning as commonly understood by those of ordinary skill in the art.

Atherosclerosis is characterized by one or more intravascular lesions formed in part of plaque including blood-borne substances such as fat, cholesterol, and calcium. An intravascular lesion such as an arterial lesion can form on a wall of an arterial lumen and build out across the lumen to an opposite wall thereof. A last point of patency often occurs at a boundary between the arterial lesion and the opposite wall of the arterial lumen. Surgical procedures for atherosclerosis such as balloon angioplasty can be used to restore patency and blood flow lost to the one or more intravascular lesions. However, a need continues to exist for medical balloons such as angioplasty balloons having a low degree of compliance, thin walls, puncture resistance, and improved trackability. Provided herein in some embodiments are systems and methods that address the foregoing.

For example, in some embodiments an apparatus is provided including a composite balloon with a tubular fiber layer and a polymeric balloon layer over the fiber layer. The composite balloon can be configured to apply a pressure to surrounding walls of an anatomical vessel in an inflated state of the composite balloon to modify one or more intravascular lesions in the anatomical vessel.

FIG. 1A provides a schematic illustrating a composite balloon 100 such as a composite balloon 100A in accordance with some embodiments.

As shown in FIG. 1A, the composite balloon 100A can include a tubular fiber layer 112A and a polymeric balloon layer 114 over the fiber layer 112A. The composite balloon 100A can include a cylindrical section 122, conical sections 124a and 124b, and neck sections 126a and 126b. The conical section 124a is a distal conical section 124a, and the conical section 124b is a proximal conical section 124b. Likewise, the neck section 126a is a distal neck section 126a, and the neck section 126b is a proximal neck section 126b. The conical sections 124a and 124b can be joined to the cylindrical section 122 through shoulders 123a and 123b, wherein the shoulder 123a is a distal shoulder 123a joining the distal conical section 124a to the cylindrical section 122, and wherein the shoulder 123b is a proximal shoulder 123b joining the proximal conical section 124b to the cylindrical section 122. The neck sections 126a and 126b can be joined to the conical sections 124a and 124b though junctions 125a and 125b, wherein the junction 125a is a distal junction 125a joining the distal neck section 126a to the distal conical section 124a, and wherein the junction 125b is a proximal junction 125b joining the proximal neck section 126b to the proximal conical section 124b.

While the composite balloon 100A is described in terms of distal portions (e.g., distal conical section 124a, distal neck section 126a, distal shoulder 123a, and distal junctions 125a) and proximal portions (e.g., proximal conical section 124b, proximal neck section 126b, proximal shoulder 123b, and proximal junction 125b), this is merely for convenience as the composite balloon 100A can be symmetric. A symmetric balloon such as the composite balloon 100A can be installed on a catheter body such as a catheter body 332 (see FIG. 3A) in any suitable orientation.

FIG. 1B provides a schematic illustrating a composite balloon 100 such as a composite balloon 100B in accordance with some embodiments.

As shown in FIG. 1B by common reference numerals, the composite balloon 100B can include many of the same features as the composite balloon 100A shown and described in reference to at least FIG. 1A; however, the composite balloon 100B differs from the composite balloon 100A in that a fiber layer 112B of the composite balloon 100B extends along the cylindrical section 122 past at least the shoulders 123a and 123b and into the conical sections 124a and 124b. The fiber layer 112B extending past at least the shoulders 123a and 123b can include, without limitation, extension of the fiber layer 112B into the conical sections 124a and 124b such as up to and including the junctions 125a and 125b.

The fiber layer 112A or 112B can be one layer of a fiber tube 212A (see FIG. 2A) including at least the one fiber layer 112A or 112B. The fiber layer 112A or 112B can be ultra high-weight polyethylene, aramid, or a combination thereof.

The fiber layer 112A or 112B can be tubularly braided or knitted with a continuous wall defining a lumen therethrough. A tubularly braided fiber layer 112A or 112B can include three or more intertwined fibers in which no two fibers are exclusively intertwined around each other. The fibers in the tubularly braided fiber layer 112A or 112B can be mechanically interlocked with each other providing unique load-distributing properties. A tubularly knitted fiber layer 112A or 112B can include intertwined fibers in a series of interconnected loops. The fibers in the tubularly knitted fiber layer 112A or 112B can also be mechanically interlocked with each other providing unique load-distributing properties. Because the fibers of the tubular fiber layer 112A or 112B can be continuous and mechanically locked, the tubular fiber layer 112A or 112B can be configured with a natural mechanism to evenly distribute a load throughout the tubular fiber layer 112A or 112B.

The balloon layer 114 can be one layer of a balloon 214 (see FIG. 2A) including at least the one balloon layer 114. The balloon layer 114 can be polyurethane, polyethylene, polyethylene terephthalate, polyether block amide, nylon, or a combination thereof.

The fiber tube 212A or the fiber layer 112A or 112B thereof can be secured to the balloon 214 or the balloon layer 114 thereof in the composite balloon 100A or 100B. The fiber tube or the fiber layer 112A or 112B thereof can include an outer surface, and the balloon 214 or the balloon layer 114 thereof can include an inner surface, which surfaces can interface and be secured to each other in the composite balloon 100A or 100B. An adhesive such as polyurethane or a solvent weld can be used to secure the outer surface of the fiber tube 212A or the fiber layer 112A or 112B thereof to the inner surface of the balloon 214 or the balloon layer 114 thereof. The composite balloon 100B can include a stronger bonding means in the conical sections 124a and 124b and adjacent thereto (e.g., the shoulders 123a and 123b, the junctions 125a and 125b, etc.) than in the cylindrical section 122. The stronger bonding means can include a higher-strength adhesive, a deeper solvent weld, or a combination thereof to obviate bond failure that might otherwise occur with a weaker bonding means.

The composite balloon 100A or 100B can be configured to withstand an inflation pressure of at least 10 atm, including at least 20 atm, such as at least 30 atm, for example, at least 40 or 50 atm.

FIG. 2A provides a schematic illustrating a method for producing a composite balloon such as the composite balloon 100A in accordance with some embodiments.

As shown, the method can include inserting a collapsed fiber tube such as a fiber tube 212A into an expanded polymeric balloon such as a polymeric balloon 214 to provide a nested intermediate 200A. The fiber tube 212A can include the fiber layer 112A, and the polymeric balloon 214 can include the balloon layer 114, each of which layers are shown and described in reference to at least FIG. 1A. The collapsed fiber tube 212A of the nested intermediate 200A can be expanded to provide an expanded fiber tube 212A in the nested intermediate 200A. The collapsed fiber tube 212A can be expanded by pushing on at least one end (e.g., a proximal or distal end) of the collapsed fiber tube 212A toward a middle of the collapsed fiber tube 212A while the other end (e.g., the distal or proximal end) of the collapsed fiber tube 212A is secured or otherwise held in place. Alternatively, the collapsed fiber tube 212A can be expanded by pushing on both ends (e.g., the proximal and distal ends) of the collapsed fiber tube 212A toward a middle of the collapsed fiber tube 212A. The expanded fiber tube 212A can be subsequently secured to the expanded polymeric balloon 214 to provide the composite balloon 100A. The expanded fiber tube 212A can include an outer surface, and the expanded polymeric balloon 214 can include an inner surface, which surfaces can interface in the nested intermediate 200. Securing the expanded fiber tube 212A to the expanded polymeric balloon 214 can include securing the outer surface of the expanded fiber tube 212A to the inner surface of the expanded polymeric balloon 214 by applying an adhesive or solvent welding the outer surface of the expanded fiber tube 212A to the inner surface of the expanded polymeric balloon 214.

FIG. 2B provides a schematic illustrating a method for producing a composite balloon such as the composite balloon 100B in accordance with some embodiments.

As shown in FIG. 2B by common reference numerals, the method for producing the composite balloon 100B can include many of the same features as the method for producing the composite balloon 100A shown and described in reference to at least FIG. 2A; however, the method for producing the composite balloon 100B differs from the method for producing the composite balloon 100A in that a collapsed fiber tube 212B including the fiber layer 112B is inserted into the expanded polymeric balloon 214 to provide a nested intermediate 200B. As shown and described in reference to at least FIG. 1B, the fiber layer 112B of the fiber tube 212B can extend along the cylindrical section 122 past at least the shoulders 123a and 123b.

FIG. 3A provides a schematic illustrating a method for producing a catheter with a composite balloon such as the composite balloon 100A in accordance with some embodiments.

As shown, the method can include inserting an elongate catheter body 332 through a center (e.g., a center along a central axis) of a composite balloon such as the composite balloon 100A to provide a nested intermediate including the composite balloon 100A and the catheter body 332. Again, the composite balloon 100A can be symmetric. Accordingly, the composite balloon 100A can be installed on the catheter body 332 in any suitable orientation. The neck sections 126a and 126b of the composite balloon 100A can be subsequently secured to a distal portion of the catheter body 332 respectively at secured sections 129a and 129b to provide at least a portion of a catheter such as an over-the-wire catheter (see FIG. 4A), a rapid-exchange catheter (see FIG. 4B), or a short rapid-exchange catheter (see FIG. 4C).

FIG. 3B provides a schematic illustrating a method for producing a catheter with a composite balloon such as the composite balloon 100B in accordance with some embodiments.

As shown in FIG. 3B by common reference numerals, the method for producing the catheter with the composite balloon 100B can include many of the same features as the method for producing the catheter with the composite balloon 100A shown and described in reference to at least FIG. 3A; however, the method for producing the catheter with the composite balloon 100B differs from the method for producing the catheter with the composite balloon 100A in the composite balloon 200B itself.

FIG. 4A provides a schematic illustrating an over-the-wire balloon catheter 400A including the composite balloon 100 in accordance with some embodiments.

As shown in FIG. 4A, the over-the-wire balloon catheter 400A can include the catheter body 332, the composite balloon 100 such as the composite balloon 100A or the composite balloon 100B (shown) over at least some of a distal portion of the catheter body 332. The over-the-wire balloon catheter 400A can further include a tip 434 of a distal end of the catheter body 332 or coupled thereto and a hub 440A at a proximal end of the catheter body 332. In addition, the over-the-wire balloon catheter 400A can be configured with a guidewire G as shown entering the over-the-wire balloon catheter 400A through a guidewire port 442A in the hub 440A of the over-the-wire balloon catheter 400A. The hub 440A can also include an inflation port 444A for attaching an inflation device for controlled inflation and deflation of the composite balloon 100 through a fluidly connected inflation lumen disposed within the catheter body 332.

FIG. 4B provides a schematic illustrating a rapid-exchange balloon catheter 400B including the composite balloon 100 in accordance with some embodiments.

As shown in FIG. 4B, the rapid-exchange balloon catheter 400B can include the catheter body 332, the composite balloon 100 such as the composite balloon 100A or the composite balloon 100B (shown) over at least some of the distal portion of the catheter body 332. The rapid-exchange balloon catheter 400B can further include the tip 434 at the distal end of the catheter body 332 or coupled thereto. The rapid-exchange balloon catheter 400B can further include a hub 440B with an inflation port 444B at the proximal end of the catheter body 332 for attaching an inflation device for controlled inflation and deflation of the composite balloon 100 through a fluidly connected inflation lumen disposed within the catheter body 332. In addition, the rapid-exchange balloon catheter 400B can be configured with a guidewire G as shown entering the rapid-exchange balloon catheter 400B through a guidewire port 442B of the rapid-exchange balloon catheter 400B. The guidewire port 442B can be in a medial portion of the catheter body 332 between the composite balloon 100 and the hub 440B.

FIG. 4C provides a schematic illustrating a short rapid-exchange balloon catheter 400C including the composite balloon 100 in accordance with some embodiments.

As shown in FIG. 4C, the rapid-exchange balloon catheter 400C can include the catheter body 332, the composite balloon 100 such as the composite balloon 100A or the composite balloon 100B (shown) over at least some of the distal portion of the catheter body 332. The short rapid-exchange balloon catheter 400C can further include the tip 434 at the distal end of the catheter body 332 or coupled thereto. The short rapid-exchange balloon catheter 400C can further include the hub 440B with the inflation port 444B at the proximal end of the catheter body 332 for attaching an inflation device for controlled inflation and deflation of the composite balloon 100 through a fluidly connected inflation lumen disposed within the catheter body 332. In addition, the short rapid-exchange balloon catheter 400C can be configured with a guidewire G as shown entering the short rapid-exchange balloon catheter 400C through a guidewire port 442C of the short rapid-exchange balloon catheter 400C. The guidewire port 442C can be in a distal portion of the catheter body 332 between the tip 434 and the composite balloon 100 or in the tip 434 itself.

Each balloon catheter of the over-the-wire balloon catheter 400A, the rapid-exchange balloon catheter 400B, and the short rapid-exchange balloon catheter 400C can be used in a system with an inflation device configured to inflate the composite balloon 100 for modification of one or more intravascular lesions. Such an inflation device can include a piston pump, a manometer, high-pressure tubing configured to tolerate pressures of at least 30 or 40 atm, and an adapter configured to connect with the hub (e.g., the hub 440A or the hub 440B) at the proximal end of the elongate body 332. In some embodiments, the inflation device is a CALIBER® Inflation Device or the PRESTO® Inflation Device by Bard Peripheral Vascular, Inc. of Tempe, Ariz.

FIG. 5 provides a schematic illustrating modification of an intravascular lesion in accordance with some embodiments.

As shown, a balloon catheter such as the over-the-wire balloon catheter 400A, the rapid-exchange balloon catheter 400B, or the short rapid-exchange balloon catheters 400C can be advanced through a patient's vasculature until the composite balloon 100 is in a position alongside an intravascular lesion L. Inflation of the composite balloon 100 in such a position can provide an outwardly focused force against the lesion L along a length of the composite balloon 100, thereby restoring patency lost to the intravascular L. The outwardly focused force can increase from a minimum when the composite balloon 100 is in an uninflated or minimally inflated state to a maximum when the composite balloon 100 is in a fully inflated state. The foregoing can be effected in vasculature of various sizes and tortuosities. The composite balloon 100 can be sufficiently flexible to modify intravascular lesions in curved vasculature.

A balloon catheter such as the over-the-wire balloon catheter 400A, the rapid-exchange balloon catheter 400B, or the short rapid-exchange balloon catheters 400C can be used to dilate stenoses in the iliac, femoral, ilio-femoral, popliteal, infra-popliteal, and renal arteries and to treat obstructive lesions of native or synthetic arteriovenous dialysis fistulae. The balloon catheter can also be used for post dilatation of balloon-expandable stents, self-expanding stents, and stent grafts in the peripheral vasculature.

As such, provided herein in some embodiments is an apparatus including a composite balloon with a tubular fiber layer and a polymeric balloon layer over the fiber layer. The composite balloon can be configured to apply a pressure to surrounding walls of an anatomical vessel in an inflated state of the composite balloon to modify one or more intravascular lesions in the anatomical vessel.

In such embodiments, the fiber layer can be ultra highweight polyethylene, aramid, or a combination thereof, and the fiber layer can be tubularly braided or knitted. In such embodiments, the balloon layer can be polyurethane, polyethylene, polyethylene terephthalate, polyether block amide, nylon, or a combination thereof. In such embodiments, the composite balloon can further include an adhesive or a solvent weld bonding the balloon layer to the fiber layer. In such embodiments, the composite balloon can further include a cylindrical section, conical sections, and shoulders between the cylindrical section and the conical sections, wherein the fiber layer can extend along the cylindrical section past at least the shoulders and into the conical sections. In such embodiments, the composite balloon can be configured to withstand an inflation pressure of at least 20 atm. In such embodiments, the composite balloon can be configured to provide an outwardly focused force along a length of the composite balloon when the composite balloon is in the inflated state. In such embodiments, the composite balloon can be sufficiently flexible to modify one or more intravascular lesions in curved vasculature when the composite balloon is in the inflated state.

Also provided herein in some embodiments is an apparatus including an elongate catheter body; an inflation lumen disposed within the catheter body; and a composite balloon. The elongate catheter body can include a distal portion and a proximal portion, and the composite balloon can be about the distal portion. The composite balloon can include a tubularly braided fiber layer and a polymeric balloon layer over the fiber layer. The composite balloon can be configured to apply a pressure to surrounding walls of an anatomical vessel in an inflated state of the composite balloon to modify one or more intravascular lesions in the anatomical vessel.

In such embodiments, the fiber layer can be ultra highweight polyethylene, aramid, or a combination thereof. In such embodiments, the balloon layer can be polyurethane, polyethylene, polyethylene terephthalate, polyether block amide, nylon, or a combination thereof. In such embodiments, the composite balloon can further include an adhesive or a solvent weld bonding the balloon layer to the fiber layer. In such embodiments, the composite balloon can further include a cylindrical section, conical sections, and shoulders between the cylindrical section and the conical sections, wherein the fiber layer extends along the cylindrical section past at least the shoulders and into the conical sections. In such embodiments, the composite balloon can be configured to withstand an inflation pressure of at least 30 atm. In such embodiments, the apparatus can further comprise a guidewire port in a hub coupled to the proximal portion for a guidewire in an over-the-wire catheter, a guidewire port in a medial portion of the catheter body between the distal portion and the proximal portion for a guidewire in a rapid-exchange catheter, or a guidewire port in a tip coupled to the distal portion for a guidewire in a short rapid-exchange catheter. In such embodiments, the apparatus can further comprise an inflation device configured to inflate the composite balloon through the inflation lumen, wherein the inflation device includes a piston pump, a manometer, high-pressure tubing configured to tolerate pressures of at least 30 atm, and an adapter configured to fluidly couple the inflation device to the inflation lumen.

Also provided herein in some embodiments is a method including inserting a collapsed fiber tube into an expanded polymeric balloon; expanding the collapsed fiber tube to provide an expanded fiber tube; and securing the expanded fiber tube to the expanded polymeric balloon. The expanded fiber tube can include an outer surface, and the expanded polymeric balloon can include an inner surface. Securing the expanded fiber tube to the expanded polymeric balloon can include securing the outer surface of the expanded fiber tube to the inner surface of the expanded polymeric balloon. Thereby, the method can include forming a composite balloon configured to apply a pressure to surrounding walls of an anatomical vessel in an inflated state of the composite balloon to modify one or more intravascular lesions in the anatomical vessel.

In such embodiments, the fiber tube can be tubularly braided or knitted, and expanding the collapsed fiber tube can include pushing on at least one end of the collapsed fiber tube toward a middle of the collapsed fiber tube. In such embodiments, the fiber tube can be ultra high-weight polyethylene, aramid, or a combination thereof. In such embodiments, the polymeric balloon can be polyurethane, polyethylene, polyethylene terephthalate, polyether block amide, nylon, or a combination thereof. In such embodiments, securing the outer surface of the expanded fiber tube to the inner surface of the expanded polymeric balloon can include applying an adhesive or solvent bonding the outer surface of the expanded fiber tube to the inner surface of the expanded polymeric balloon. In such embodiments, the method can further comprise inserting a distal portion of an elongate catheter body through a center of the composite balloon and securing the composite balloon to the distal portion of the catheter body.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. An apparatus, comprising:
    a composite balloon including:
        a fiber tube comprising a hollow cylindrical body formed of fibers without an inner support layer;
        a polymeric balloon over the fiber tube, and
        an adhesive or a solvent securing the the fiber tube to an inner surface of the polymeric balloon;
        wherein the composite balloon is configured to apply a pressure to surrounding walls of an anatomical vessel in an inflated state of the composite balloon to modify one or more intravascular lesions in the anatomical vessel.

2. The apparatus of claim 1, wherein the fiber tube is ultra high-weight polyethylene, aramid, or a combination thereof, and wherein the fiber tube is tubularly braided or knitted.

3. The apparatus of claim 1, wherein the balloon is polyurethane, polyethylene, polyethylene terephthalate, polyether block amide, nylon, or a combination thereof.

4. The apparatus of claim 1, wherein the composite balloon further includes a cylindrical section, conical sections, and shoulders between the cylindrical section and the conical sections, and wherein the fiber tube extends only along the cylindrical section.

5. The apparatus of claim 1, wherein the composite balloon is configured to withstand an inflation pressure of at least 20 atm.

6. The apparatus of claim 1, wherein the composite balloon is configured to provide an outwardly focused force along a length of the composite balloon when the composite balloon is in the inflated state.

7. The apparatus of claim 1, wherein the composite balloon is sufficiently flexible to modify one or more intravascular lesions in curved vasculature when the composite balloon is in the inflated state.

8. The apparatus of claim 1, wherein the fiber tube extends along a conical section of the composite balloon.

9. An apparatus, comprising:
    an elongate catheter body including a distal portion and a proximal portion;
    an inflation lumen disposed within the catheter body; and
    a composite balloon about the distal portion including:
        a braided fiber tube; and
        a polymeric balloon over the fiber tube; and
        an adhesive or a solvent securing the fiber tube to an inner surface of the polymeric balloon;
        wherein the composite balloon is configured to apply a pressure to surrounding walls of an anatomical vessel in an inflated state of the composite balloon to modify one or more intravascular lesions in the anatomical vessel.

10. The apparatus of claim 9, wherein the fiber layer is ultra high-weight polyethylene, aramid, or a combination thereof.

11. The apparatus of claim 9, wherein the balloon is polyurethane, polyethylene, polyethylene terephthalate, polyether block amide, nylon, or a combination thereof.

12. The apparatus of claim 9, wherein the composite balloon further includes a cylindrical section, conical sections, and shoulders between the cylindrical section and the conical sections, and wherein the fiber tube extends only along the cylindrical section.

13. The apparatus of claim 9, wherein the composite balloon is configured to withstand an inflation pressure of at least 30 atm.

14. The apparatus of claim 9, further comprising:
    a guidewire port in a hub coupled to the proximal portion for a guidewire in an over-the-wire catheter,
    a guidewire port in a medial portion of the catheter body between the distal portion and the proximal portion for a guidewire in a rapid-exchange catheter, or
    a guidewire port in a tip coupled to the distal portion for a guidewire in a short rapid-exchange catheter.

15. The apparatus of claim 9, further comprising:
    an inflation device configured to inflate the composite balloon through the inflation lumen,
    wherein the inflation device includes a piston pump, a manometer, high-pressure tubing configured to tolerate pressures of at least 30 atm, and an adapter configured to fluidly couple the inflation device to the inflation lumen.

16. The apparatus of claim 9, wherein the braided fiber tube extends along a conical section of the composite balloon.

17. A method, comprising:
    inserting a collapsed fiber tube into an expanded polymeric balloon;
    expanding the collapsed fiber tube to provide an expanded fiber tube comprising a hollow cylindrical body formed of fibers without an inner support layer,
    wherein an outer surface of the expanded fiber tube interfaces an inner surface of the expanded polymeric balloon; and securing the outer surface of the expanded fiber tube to the inner surface of the expanded polymeric balloon, thereby forming a composite balloon configured to apply a pressure to surrounding walls of an anatomical vessel in an inflated state of the composite balloon to modify one or more intravascular lesions in the anatomical vessel.

18. The method of claim 17, wherein the fiber tube is tubularly braided or knitted, and wherein expanding the collapsed fiber tube includes pushing on at least one end of the collapsed fiber tube toward a middle of the collapsed fiber tube.

19. The method of claim 17, wherein the fiber tube is ultra high-weight polyethylene, aramid, or a combination thereof, wherein the polymeric balloon is polyurethane, polyethylene, polyethylene terephthalate, polyether block amide, nylon, or a combination thereof, and wherein securing the outer surface of the expanded fiber tube to the inner surface of the expanded polymeric balloon includes applying an adhesive or solvent bonding the outer surface of the expanded fiber tube to the inner surface of the expanded polymeric balloon.

20. The method of claim 17, further comprising:

inserting a distal portion of an elongate catheter body through a center of the composite balloon; and securing the composite balloon to the distal portion of the catheter body.

21. A method, comprising:

inserting a collapsed fiber tube into an expanded polymeric balloon;

expanding the collapsed fiber tube to provide an expanded fiber tube, wherein an outer surface of the expanded fiber tube interfaces an inner surface of the expanded polymeric balloon; and securing the outer surface of the expanded fiber tube to the inner surface of the expanded polymeric balloon, thereby forming a composite balloon configured to apply a pressure to surrounding walls of an anatomical vessel in an inflated state of the composite balloon to modify one or more intravascular lesions in the anatomical vessel, wherein the fiber tube is tubularly braided or knitted, and wherein expanding the collapsed fiber tube includes pushing on at least one end of the collapsed fiber tube toward a middle of the collapsed fiber tube.

* * * * *

UNITED STATES PATENT AND TRADEMARK OFFICE
CERTIFICATE OF CORRECTION

| | | |
|---|---|---|
| PATENT NO. | : 11,660,428 B2 | Page 1 of 1 |
| APPLICATION NO. | : 16/469344 | |
| DATED | : May 30, 2023 | |
| INVENTOR(S) | : Karen A. DiClaudio | |

It is certified that error appears in the above-identified patent and that said Letters Patent is hereby corrected as shown below:

In the Claims

Column 9, Claim 1, Line 47, please delete "the the fiber" and insert -- the fiber --.

Column 10, Claim 9, Line 16, please delete "tube; and" and insert -- tube; --.

Column 10, Claim 10, Line 25, please delete "fiber layer" and insert -- fiber tube --.

Signed and Sealed this
Eleventh Day of November, 2025

John A. Squires
*Director of the United States Patent and Trademark Office*